United States Patent
Sprencz et al.

(10) Patent No.: US 9,424,644 B2
(45) Date of Patent: *Aug. 23, 2016

(54) METHODS AND SYSTEMS FOR EVALUATING BONE LESIONS

(71) Applicant: General Electric Company, Schenectady, NY (US)

(72) Inventors: Pal Csongor Sprencz, Budapest (HU); Robert John Johnsen, Pewaukee, WI (US); Istvan Ubelhart, Budapest (HU); Elizabeth Philps, Hartland, WI (US); Andras Kriston, Mako (HU); Andrea Fazekas, Budapest (HU)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/043,938

(22) Filed: Feb. 15, 2016

(65) Prior Publication Data

US 2016/0171687 A1 Jun. 16, 2016

Related U.S. Application Data

(63) Continuation of application No. 14/013,087, filed on Aug. 29, 2013.

(51) Int. Cl.
*G06T 7/00* (2006.01)
*G06F 19/00* (2011.01)
(Continued)

(52) U.S. Cl.
CPC ............ *G06T 7/0012* (2013.01); *A61B 5/4504* (2013.01); *G06T 7/0081* (2013.01); *G06T 2200/24* (2013.01); *G06T 2207/10081* (2013.01); *G06T 2207/10088* (2013.01); *G06T 2207/10104* (2013.01); *G06T 2207/20148* (2013.01); *G06T 2207/20224* (2013.01); *G06T 2207/30008* (2013.01)

(58) Field of Classification Search
None
See application file for complete search history.

(56) References Cited

U.S. PATENT DOCUMENTS

| 4,941,474 A | 7/1990 | Pratt, Jr. |
| 6,213,958 B1 | 4/2001 | Winder |

(Continued)

OTHER PUBLICATIONS

Ohlsson et al. "Automated Decision Support for Bone Scintigraphy," published in Aug. 2009 at Computer-Based Medical Systems, 2009. CBMS 2009. 22nd IEEE International Symposium, 17 pages.

(Continued)

*Primary Examiner* — Nirav G Patel
*Assistant Examiner* — Alexander J Lesnick
(74) *Attorney, Agent, or Firm* — Hanley, Flight and Zimmerman, LLC

(57) ABSTRACT

Methods and systems for evaluating bone lesions include accessing a first dataset acquired from a patient with a first imaging modality and a second dataset acquired from the patient with a second imaging modality. A segmentation is performed on the first dataset to identify a subset of the first dataset corresponding to a skeletal structure of the patient and a patient skeletal metric representing a total bone volume of the patient is automatically calculated from the subset of the first dataset. The methods and systems further include detection of at least one lesion in the second dataset, classification of the at least one lesion as a bone or non-bone lesion, automatic calculation of a bone lesion metric based on the classification, and calculation of a lesion burden as a ratio of the bone lesion metric and the patient skeletal metric.

20 Claims, 7 Drawing Sheets

(51) Int. Cl.
  *G06K 9/00*     (2006.01)
  *A61B 6/00*     (2006.01)
  *A61B 6/03*     (2006.01)
  *A61B 5/00*     (2006.01)
  *A61B 17/34*    (2006.01)
  *A61B 8/08*     (2006.01)
  *A61B 6/12*     (2006.01)

(56) References Cited

U.S. PATENT DOCUMENTS

| | | |
|---|---|---|
| 7,796,795 B2 | 9/2010 | Uppaluri et al. |
| 8,094,906 B2 | 1/2012 | Porat et al. |
| 2008/0049999 A1 | 2/2008 | Jerebko et al. |
| 2009/0226060 A1* | 9/2009 | Gering ............... G06T 7/0081 382/128 |
| 2010/0032575 A1 | 2/2010 | Iagaru et al. |
| 2011/0007954 A1* | 1/2011 | Suehling ........... G06K 9/00362 382/128 |
| 2012/0183193 A1* | 7/2012 | Wels .................. G06K 9/4614 382/131 |
| 2013/0094704 A1* | 4/2013 | Hamadeh ............. G06N 3/02 382/103 |
| 2014/0010428 A1* | 1/2014 | Schmidt ............. A61B 5/0033 382/131 |
| 2014/0105471 A1 | 4/2014 | Brown |
| 2014/0276035 A1* | 9/2014 | Jeraj .................. A61B 5/4848 600/431 |
| 2014/0330170 A1* | 11/2014 | Holland ............. A61B 6/032 600/587 |
| 2015/0063667 A1 | 3/2015 | Sprencz et al. |

OTHER PUBLICATIONS

United States Patent and Trademark Office, "Notice of Allowance", issued in connection with U.S. Appl. No. 14/013,087, mailed on Jan. 4, 2016, 19 pages.

United States Patent and Trademark Office, "Final office action", issued in connection with U.S. Appl. No. 14/013,087, mailed on Oct. 6, 2015, 17 pages.

United States Patent and Trademark Office, "Corrected Notice of Allowability", issued in connection with U.S. Appl. No. 14/013,087, mailed on Feb. 3, 2016, 4 pages.

United States Patent and Trademark Office, "Non-Final office action", issued in connection with U.S. Appl. No. 14/013,087, mailed on Apr. 8, 2015, 36 pages.

\* cited by examiner

METHODS AND SYSTEMS FOR EVALUATING BONE LESIONS

RELATED APPLICATION

This patent arises from a continuation of U.S. application Ser. No. 14/013,087 (Now U.S. Pat. No. 9,324,140), entitled "METHODS AND SYSTEMS FOR EVALUATING BONE LESIONS", which was filed on Aug. 29, 2013 and is hereby incorporated herein by reference in its entirety.

BACKGROUND OF THE INVENTION

Embodiments of the invention relate generally to medical diagnostics and treatment assessment and, more particularly, to methods and systems for evaluating bone lesions using multi-modality image data.

It is not uncommon for a single patient to undergo a multitude of medical imaging exams, whether in a single doctor's visit, in a hospital stay, or even over the course of a lifetime. This is particularly likely when a patient undergoes a series of "tests" and scans to investigate a recently onset or previously undetected condition. It is increasingly common for a patient to be subjected to multiple scans across multiple medical imaging modalities because each exam can provide different pieces of information. For example, during a single doctor's visit or hospital stay, a magnetic resonance (MR) imaging system, an x-ray imaging system, or a computed tomography (CT) imaging system can be used to acquire images that provide anatomical information, while a positron emission tomography (PET) imaging system or functional MRI can be used to acquire images that provide functional information. The anatomical information providing insight into the anatomical makeup of the patient and the functional information providing insight into the functionality of a given anatomical structure, especially when subjected to a stimulus. Moreover, the combination of anatomical and functional information is not only advantageous in detecting a new pathology or abnormality, but the respective images, when taken over the course of an illness, for example, may show growth of lesions, responses to treatments, and disease progression. To assist in the analysis of anatomical and functional information, programs have been constructed that register an anatomical and a functional image thereby showing, in a single image, both anatomical and functional information.

Many clinical applications analyze 2D or 3D image data to perform and capture quantitative analytics. These include detection and sizing of lung nodules (Advanced Lung Analysis), quantification of vessel curvature, diameter, and tone (Advanced Vessel Analysis), cardiac vascular and function applications, navigating of the colon for detection of polyps (CT colonography), detection and sizing of lesions, and the like. Dedicated CT, MR, PET and nuclear medicine applications have been designed to output quantitative analytics from regions of interest (intensity, density (HU), standard uptake value (SUV), distances, volumes, growth rates, pattern and/or texture recognition, functional information, etc.) to help in the diagnosis and management of patients.

Quantification of bone lesions using medical images is an important aspect of clinical diagnostics and therapy. Information related to the quantity or overall volume of bone lesions detected in a patient may be used by medical practitioners to select the best course of treatment for a patient and to monitor treatment efficiency and collect relevant research data.

Conventional methods of quantifying bone lesions in a patient utilize a reference value as an estimate of the volume of a particular patient's skeletal structure. Because this reference value is a quantitative value selected from tabular reference data based on the demographics (e.g., age, sex, height, etc.) of the patient, the reference value may not accurately reflect the actual skeletal volume of the patient.

Lesions within the skeletal structure of the patient are detected by first manually segmenting the skeletal structure from image data acquired from the patient and manually identifying lesions within the segmentation. The manual segmentation of the skeletal structural and manual detection of lesions is very challenging due to the complexity of the skeletal structure. For example, the anatomy and composition of bone material can vary significantly among patients, which can lead to significant inter-operator variability.

Further, the segmentation of the skeletal structure typically includes the brain, which can cause inaccurate quantitative analytics of the skeletal structure, and in turn affects a practitioner's ability to efficiently and accurately acquire measurements and data to assess the patient's condition.

Therefore, it would be desirable to have a system and method of quantifying bone lesions that overcomes the aforementioned drawbacks.

BRIEF DESCRIPTION OF THE INVENTION

In accordance with one aspect of the present invention, a non-transitory computer readable storage medium has stored thereon a computer program and represents a set of instructions that when executed by the computer causes the computer to access a first set of data of a first data type and access a second set of data of a second data type. The first set of data is acquired from a patient with a first imaging modality, and the second set of data is acquired from the patient with a second imaging modality. The set of instructions also causes the computer to perform a segmentation on the first set of data to identify a subset of the first set of data corresponding to a skeletal structure of the patient. Further, the set of instructions causes the computer to automatically calculate a patient skeletal metric from the subset of the first set of data, the patient skeletal metric representing a total bone volume of the patient. In addition, the set of instructions causes the computer to detect at least one lesion in the second set of data, classify the at least one lesion as a one of a bone lesion and a non-bone lesion, and automatically calculate a bone lesion metric based on the classification. The set of instructions further causes the computer to calculate a lesion burden as a ratio of the bone lesion metric and the patient skeletal metric.

According to another aspect of the invention, a method includes accessing an anatomical image data set acquired from a patient and accessing a function image data set acquired from the patient. The method also includes identifying a subset of the anatomical image dataset corresponding to bone and calculating a skeletal volume from the subset of the anatomical image dataset. In addition, the method includes identifying a set of lesions from the function image dataset, comparing the set of lesions to the subset of the anatomical image dataset to identify at least one bone lesion within the set of lesions, automatically calculating a bone lesion burden based on the at least one bone lesion. Further, the method includes calculating a bone lesion index from the bone lesion burden and the skeletal volume.

In accordance with another aspect of the invention, a medical diagnostic tool includes an image acquisition system configured to acquire multi-modality image data, a first database having stored thereon a first image dataset acquired from a patient using a first imaging modality, a second database having stored thereon a second image dataset acquired from the patient using a second imaging modality, and a computer processor. The computer processor is programmed to access the first and second image datasets. The computer processor is further programmed to segment the first image dataset to define a set of skeletal data, identify a location of a lesion candidate in the second image set, compare the location of the lesion candidate to the set of skeletal data, and classify the lesion candidate as one of a bone lesion and a non-bone lesion based on the comparison to define a set of bone lesion data. In addition, the computer processor is programmed to calculate a lesion burden based on a ratio of the set of bone lesion data and the set of skeletal data. The medical diagnostic tool also includes a graphical user interface (GUI) constructed to display an image generated from overlaying a first image corresponding to the set of skeletal data on a second image corresponding to the set of bone lesion data.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of embodiments of the invention is described below with respect to a multi-modality imaging system that includes a positron emission tomography (PET) imaging system and one of an magnetic resonance (MR) imaging system and a sixty-four-slice, "third generation" computed tomography (CT) imaging system. However, it will be appreciated by those skilled in the art that the invention is equally applicable for use with other multi-slice configurations and with other CT imaging systems. In addition, while embodiments of the invention are described with respect to techniques for use with MR or CT imaging systems and PET imaging systems, one skilled in the art will recognize that the concepts set forth herein are not limited to CT and PET and can be applied to techniques used with other imaging modalities in both the medical field and non-medical field, such as, for example, an x-ray system, a single-photon emission computed tomography (SPECT) imaging system, or any combination thereof.

Figure 1:
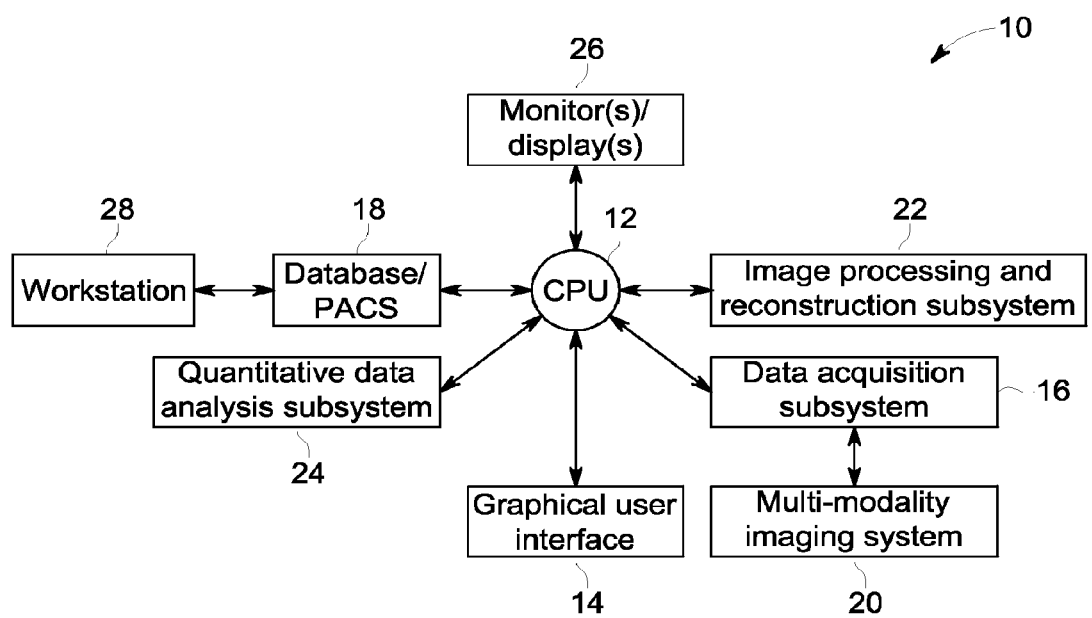
FIG. 1 is a schematic diagram of a medical imaging system according to one embodiment of the invention.
Figure 2:
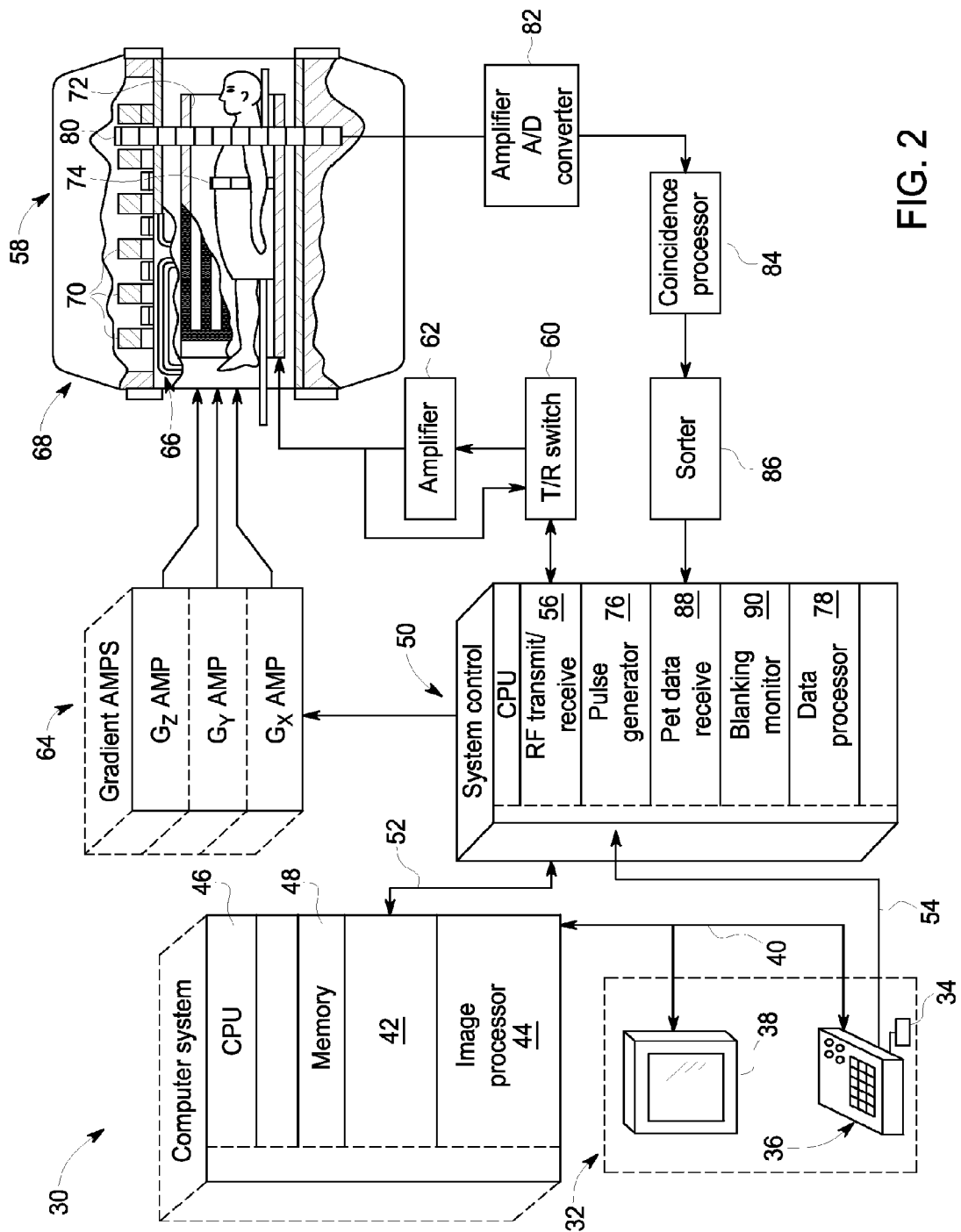
FIG. 2 is a schematic block diagram of an exemplary multi-modality medical imaging system, useable with the medical imaging system of FIG. 1, which includes a PET imaging system and a MR imaging system.
Figure 3:
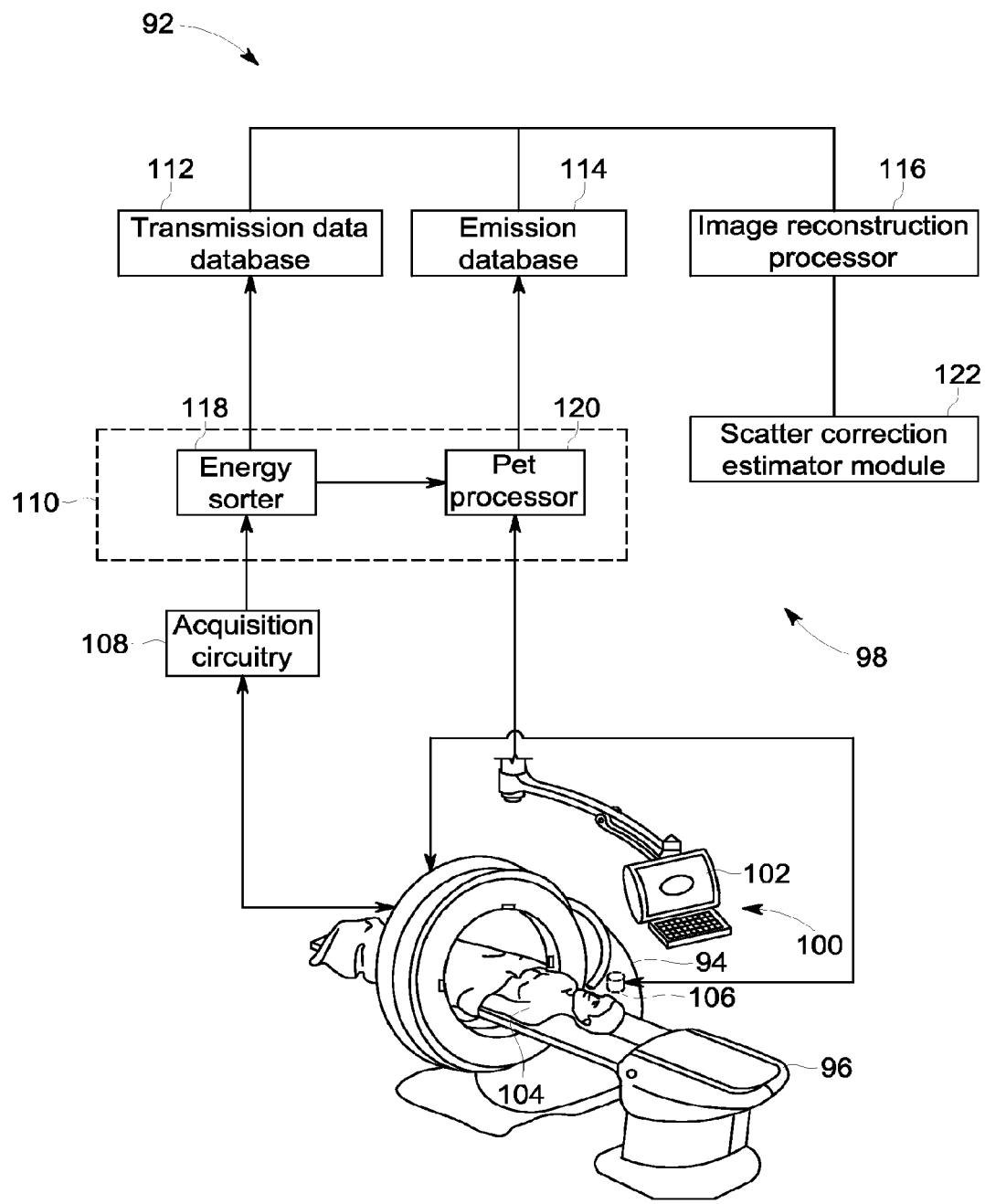
FIG. 3 is a schematic block diagram of an exemplary multi-modality medical imaging system, useable with the medical imaging system of FIG. 1, which includes a PET imaging system and a CT imaging system.

Referring now to FIG. 1, an exemplary imaging system 10 for use with embodiments of the present invention is shown. The imaging system 10 is not modality specific. In this regard, the system 10 includes a central processor (CPU) 12 that controls operation of the system 10. The imaging system 10 further includes a graphical user interface (GUI) 14 that allows an operator to prescribe a scan and interact with the collected data and images. Data acquisition is controlled, via the CPU 12, by data acquisition subsystem 16. According to various embodiments, data acquisition subsystem 16 may access previously acquired data stored in database 18 or may acquire data directly from a multi-modality imaging subsystem 20. Multi-modality imaging subsystem 20 may be a combined PET/MR system (as shown in FIG. 2), a combined PET/CT system (as shown in FIG. 3), a combined SPECT/MR system, or a combined SPECT/CT system, as non-limiting examples.

Imaging system 10 further includes an image processing and reconstruction subsystem 22 that generates reconstructed images as well a quantitative data analysis subsystem 24 that derives quantitative data from data collected from data acquisition system 16. The reconstructed images generated by image processing and reconstruction subsystem 22 and the quantitative data computed or otherwise derived from quantitative data analysis subsystem 24 may be stored in database 18. Additionally, it is contemplated that database 18 may be more than one database and remotely located from the site of data acquisition.

System 10 further has one or more displays 26 to visually display images and quantitative data as set forth herein. One having skill in the art will appreciate that that system 10 may include other software, firmware, and hardware not specifically described to prescribe and execute a given scan, as well as processing the data for image reconstruction and quantitative analysis.

Additionally, it is contemplated that a dedicated workstation 28 having a computer, monitor(s), and operably connected to the one or more databases may be used such that a physician may analyze the image and quantitative data remote from the scanner. As such, it is understood that systems and methods described herein may be used remotely from the treatment facility at which the patient is scanned.

FIG. 2 illustrates an exemplary PET/MR imaging system 30 useable with multi-modality imaging subsystem 20. The operation of PET/MR imaging system 30 may be controlled from an operator console 32, which includes a keyboard or other input device 34, a control panel 36, and a display 38. The console 32 communicates though a link 40 with a separate computer system 42 that enable an operator to control the production and display of images on the display 38. The computer system 42 includes a number of modules, such as an image processor module 44, a CPU module 46, and a memory module 48. The computer system 42 may also be connected to permanent or back-up memory storage, a network, or may communicate with a separate system control 50 through link 52. The input device 34 can include a mouse, keyboard, track ball, touch activated screen, light wand, or any similar or equivalent input device, and may be used for interactive geometry prescription.

The system control 50 includes a set of modules in communication with one another and connected to the operator console 32 through link 54. It is through link 52 that the system control 50 receives commands to indicate the scan sequence or sequences that are to be performed. For MR data acquisition, an RF transmit/receive module 56 commands a scanner 58 to carry out the desired scan sequence, by sending instructions, commands, and/or requests describing the timing, strength, and shape of the RF pulses and pulse sequences to be produced, to correspond to the timing and length of the data acquisition window. In this regard, a transmit/receive switch 60 controls the flow of data via an amplifier 62 to scanner 58 from RF transmit module 56 and from scanner 58 to RF receive module 56. The system control 50 also connects to a set of gradient amplifiers 64, to indicate the timing and shape of the gradient pulses that are produced during the scan.

The gradient waveform instructions produced by system control 50 are sent to the gradient amplifier system 64 having Gx, Gy, and Gz amplifiers. Amplifiers 64 may be external of scanner 58 or system control 50, or may be integrated therein. Each gradient amplifier excites a corresponding physical gradient coil in a gradient coil assembly 66 to produce the magnetic field gradients used for spatially encoding acquired signals. The gradient coil assembly 66 forms part of a magnet assembly 68, which includes a polarizing magnet 70 and an RF coil assembly 72, 74. Alternatively, the gradient coils of gradient coil assembly 66 may be independent of the magnet assembly 68. RF coil assembly may include a whole-body RF transmit coil 72 as shown, surface or parallel imaging coils 74, or a combination of both. The coils 72, 74 of the RF coil assembly may be configured for both transmitting and receiving, or for transmit-only or receive-only. A pulse generator 76 may generate PET data blanking signals synchronously with the production of the pulse sequences. These blanking signals may be generated on separate logic lines for subsequent data processing. The MR signals resulting from the excitation pulses, emitted by the excited nuclei in the patient, may be sensed by the whole body coil 72 or by separate receive coils, such as parallel coils or surface coils 74, and are then transmitted to the RF transmit/receive module 56 via the transmit/receive switch 60. The MR signals are demodulated, filtered, and digitized in a data processing section 78 of the system control 50.

An MR scan is complete when one or more sets of raw k-space data has been acquired in the data processor 78. This raw k-space data is reconstructed in data processor 78, which operates to transform the data (through Fourier or other techniques) in image data. This image data is conveyed through link 52 to the computer system 42, where it is stored in memory 48. Alternatively, in some systems computer system 42 may assume the image data reconstruction and other functions of data processor 78. In response to commands received from the operator console 32, the image data stored in memory 48 may be archived in long term storage or may be further processed by the image processor 44 or CPU 46 and conveyed to the operator console 32 and presented on the display 38.

In combined PET/MR imaging systems, PET data may be acquired simultaneously with the MR data acquisition described above. Thus, scanner 58 also contains a positron emission detector 80, configured to detect gamma rays from positron annihilations emitted from a subject. Detector 80 preferably includes a plurality of scintillators and photovoltaics arranged about a gantry. Detector 80 may, however, be of any suitable construction for acquiring PET data. Gamma ray incidences detected by detector 80 are transformed, by the photovoltaics of the detector 80, into electrical signals and are conditioned by a series of front-end electronics 82. These conditioning circuits 82 may includes various amplifies, filters, and analog-to-digital converters. The digital signals output by front-end electronics 82 are then processed by a coincidence processor 84 to match gamma ray detections as potential coincidence events. When two gamma rays strike detectors approximately opposite one another, it is possible, absent the interactions of random noise and signal gamma ray detections, that a positron annihilation took place somewhere along the line between the detectors. Thus, the coincidences determined by coincidence processor 84 are sorted into true coincidence events and are ultimately integrated by data sorter 86. The coincidence event data, or PET data, from data sorter 86 is received by the system control 50 at a PET data receive port 88 and stored in memory 48 for subsequent processing 78. PET images may then be reconstructed by image processor 44 and may be combined with MR images to produce hybrid structural and metabolic or functional images. Front-end electronics 82, coincidence processor 84, and data sorter 86 may each be external of scanner 58 or system control 50, or may be integrated therein.

A blanking control or monitor 90 is also included in system control 50. Blanking monitor 90 identified and records times during which MR components 66-72 are active or transmitting. Blanking monitor 90 may use this timing data to gate PET data acquisition by detector 80 or signal conditioning by front-end electronics 82, or may output a timing sequence to be applied during data processing by coincidence processor 84, data sorter 86, data processor 78, or image reconstructor 44.

Referring now to FIG. 3, a PET/CT imaging system 92, useable with multi-modality imaging subsystem 20 of FIG. 1 is shown. It should be noted that in some embodiments, PET/CT imaging system 92 acquires CT data prior to obtaining the PET data. However, one skilled in the art will recognize that the PET and CT data may be acquired in different orders and combinations thereof (e.g., in an interleaved manner).

PET/CT imaging system 92 generally includes a gantry 94, a patient table 96, and a processing and control system 98 including a user input 100 with a display 102. The gantry 94 provides mechanical support for imaging devices such as, for example, detectors, scanners, and transmitters that are used for scanning a patient 104. The gantry 94 houses imaging devices such as, for example, PET detectors or x-ray detectors. It should be noted that the PET system may be a stationary annular detector or optionally may include a pin source.

In some embodiments, gantry 94 includes a plurality of PET detectors that are fixed and spaced on the gantry 94, which are positioned radially outward from the axis. In accordance with other embodiments, the gantry 94 includes a plurality of detectors that are rotatable about the axis. For CT imaging, a rotating detectors and a source, for example, an x-ray tube 106 may be provided and optionally including a stationary detector ring for CT imaging may be provided. In other embodiments, a separate imaging gantry is provided for CT imaging.

The imaging devices on the gantry 94 acquire image data by scanning the patient 104 lying on the patient table 96. The patient table 96 lies along the axis of the gantry 94, and can be moved along this axis. Moving the patient table 96 enables the scanning of various portions of the patient 104. The patient table 96 can be positioned at various axial positions along the axis.

The processing and control system 98 controls the positioning of the patient table 96, and receives image data collected during scanning. In various embodiments, the processing and control system 98 controls the PET/CT imaging system 92 to acquire both emission and transmission image data of a volume of interest. For example, annihilation events may be detected as emission data, as well as transmission data from signal transmitted by a transmission source, such as the x-ray tube 106, which pass through the volume of interest of the patient 104. The transmission signals may get attenuated when the signals pass through the volume of interest and the detectors may collect data that is attenuated after the transmission signals pass through the patient 104.

Various processors, sorters, and databases are used to acquire and manipulate emission and transmission data, which is used in accordance with various embodiments. The processors, sorters, and databases of FIG. 3 include acquisition circuitry 108, an acquisition processor 110, a transmission data database 112, an emission data database 114, and an image reconstruction processor 116. The acquisition processor 110 is programmed to acquire emission data and generate an image based on the emission data acquired. Other computing components also may be included.

In some embodiments, an energy sorter 118 provides, for example, time, location, and energy data to a PET processor 120. The PET processor 120 generally uses the received data to identify pairs of data, also known as coincidence pairs, coincident pair lines, and lines of response, corresponding to annihilation events that occurred inside the region of interest. After acquisition processor 110 identifies an annihilation event, the acquisition processor 110 updates data in the emission data database 114 to store information relating to the annihilation event. CT data is also stored in the transmission data database 112 based on transmission signals that pass through the patient 104 and are detected.

Thus, after an acquisition session has been completed and sets of transmission and emission data have been stored in databases 112 and 114, respectively, image reconstruction processor 116 accesses the data in the databases 112 and 114 and uses the accessed data to generate images that may be requested by a system operator. Additionally, the sets of transmission and emission data are used by a scatter correction estimator module 122 to estimate scatter for the emission data based on both the transmission and emission data.

Figure 4:
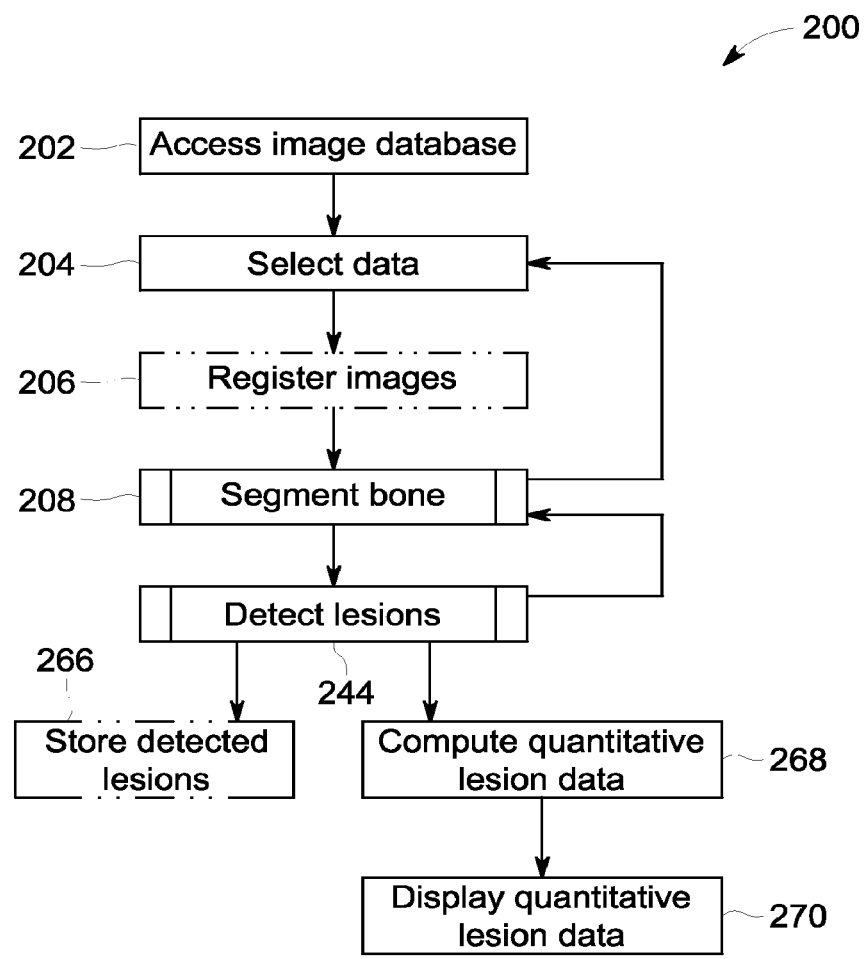
FIG. 4 is a flowchart setting forth the steps of a technique for quantifying bone lesions using multi-modality image data according to one embodiment of the invention.

FIG. 4 sets forth a technique 200 for quantifying bone lesions in a patient using multi-modality three dimensional image data. According to various embodiments, technique 200 is performed by a computer processor such as, for example, CPU12 of FIG. 1. Technique 200 begins with step 202, by selecting and loading one or more exams to be processed by the computer system corresponding to one or more imaging sessions during which multi-modality image data was acquired from a patient of interest. The multi-modality image data includes at least one set of anatomical image data acquired from the patient using an anatomical imaging modality, such as CT or MR for example, and at least one set of functional image data acquired from the patent using a functional imaging modality, such as PET or SPECT as examples. In the exemplary embodiment described below wherein the multi-modality image data includes three-dimensional CT and PET data, one CT series and one PET series from one of the loaded exams is selected in step 204. In alternative embodiments, one MR series and one PET series, one CT series and one SPECT series, and/or one MR series and one SPECT series may be selected from the loaded exams in step 204.

In optional step 206 (shown in phantom) technique 200 performs a registration of the image data of the CT and PET series in order to accurately overlay the anatomical and functional image data. Alternatively, in embodiments where the multi-modality image data is acquired from a combined PET/CT or a combined PET/MR imaging system, the acquired multi-modality image data may be automatically registered.

During step 208 an automatic bone segmentation is performed on the anatomical image data (e.g., data corresponding to the CT volume) using a bone segmentation subroutine 210 described in detail below with respect to FIG. 5. In one embodiment, a patient skeletal image representing the skeleton of the patient is generated from a subset of the anatomical image data during step 208 based on the automatic bone segmentation.

Figure 5:
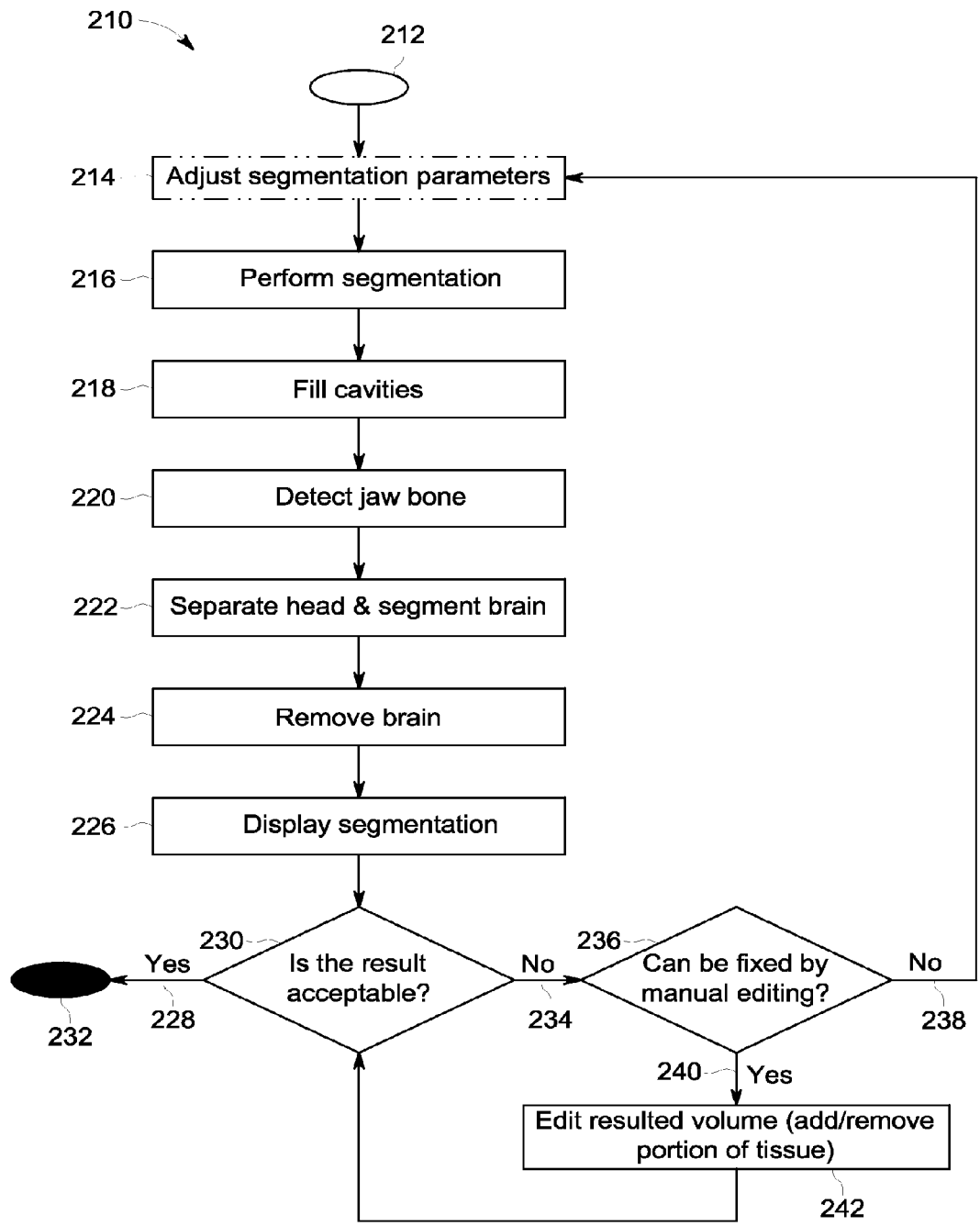
FIG. 5 is a flowchart setting forth the steps of a bone segmentation subroutine of the technique of FIG. 4 according to one embodiment of the invention.

Referring to FIG. 5, the bone segmentation subroutine 210 of technique 200 is described in detail. As shown, bone segmentation subroutine 210 begins at step 212 by accessing the anatomical image series, such as a CT series, selected at step 204 of technique 200. In optional step 214 (shown in phantom) one or more views of the accessed image series is displayed on a user interface, such as on workstation 28 of FIG. 1, to permit a user to review the image series and adjust the segmentation parameters. In step 216 bone segmentation subroutine 210 performs an automated segmentation to identify and define the skeletal structure within the anatomical image series using predefined segmentation parameters and/or the adjusted segmentation parameters defined in step 214.

In embodiments where the anatomical image series includes CT data, bone segmentation subroutine 210 uses a thresholding technique to segment the image data. The thresholding technique may, for example, define image data having attenuation values within a predetermined range as corresponding to skeletal or bone material. In embodiments where the anatomical image series includes MR data, bone segmentation subroutine 210 segments the image data based on general CT anatomy atlas mapping or using ultrashort echo time sequences generated MR data, where with a thresholding algorithm the skeleton of the bone structure can be obtained. While various segmenting techniques are described herein, one having skill in the art will recognize that embodiments of the invention may segment different anatomical region bone structures using alternative techniques, such as, for example, clustering, level set, and region growing.

After performing the automated segmentation, bone segmentation subroutine 210 fills the cavities on the defined bone structure to add the bone marrow, the spinal-cord, and the brain in step 218. In step 220 the jaw-bone is detected based on the bone/soft tissue ratio in order to eventually remove the brain. Bone segmentation subroutine 210 uses the detected jaw-bone to separate the whole head and segment the brain in step 222. The segmented brain is removed from the anatomical image data in step 224. Bone segmentation subroutine 210 then generates a patient skeleton image from a subset of the anatomical image data representing the bone of the patient and displays the image in one or more views at step 226 for user review.

If the segmentation is deemed acceptable 228 at decision block 230, the bone segmentation subroutine 210 outputs the segmented skeletal structure of the patient and ends at block 232. If the segmentation is not acceptable 234, bone segmentation subroutine 210 proceeds to decision block 236 to determine whether the segmentation can be corrected by manual editing. If the segmentation cannot be corrected by manual editing 238, bone segmentation subroutine 210 returns to step 214 to adjust the segmentation parameters and restart the segmentation process. If the segmentation can be corrected by manual editing 240, bone segmentation subroutine 210) proceeds to step 242, wherein a user manually edits the current results of the segmentation, such as by modifying the contours of the resulting skeletal structure. After the manual editing procedure is complete, bone segmentation subroutine 210 returns to decision block 230 to determine whether the result of the edited segmentation is acceptable.

Figure 6:
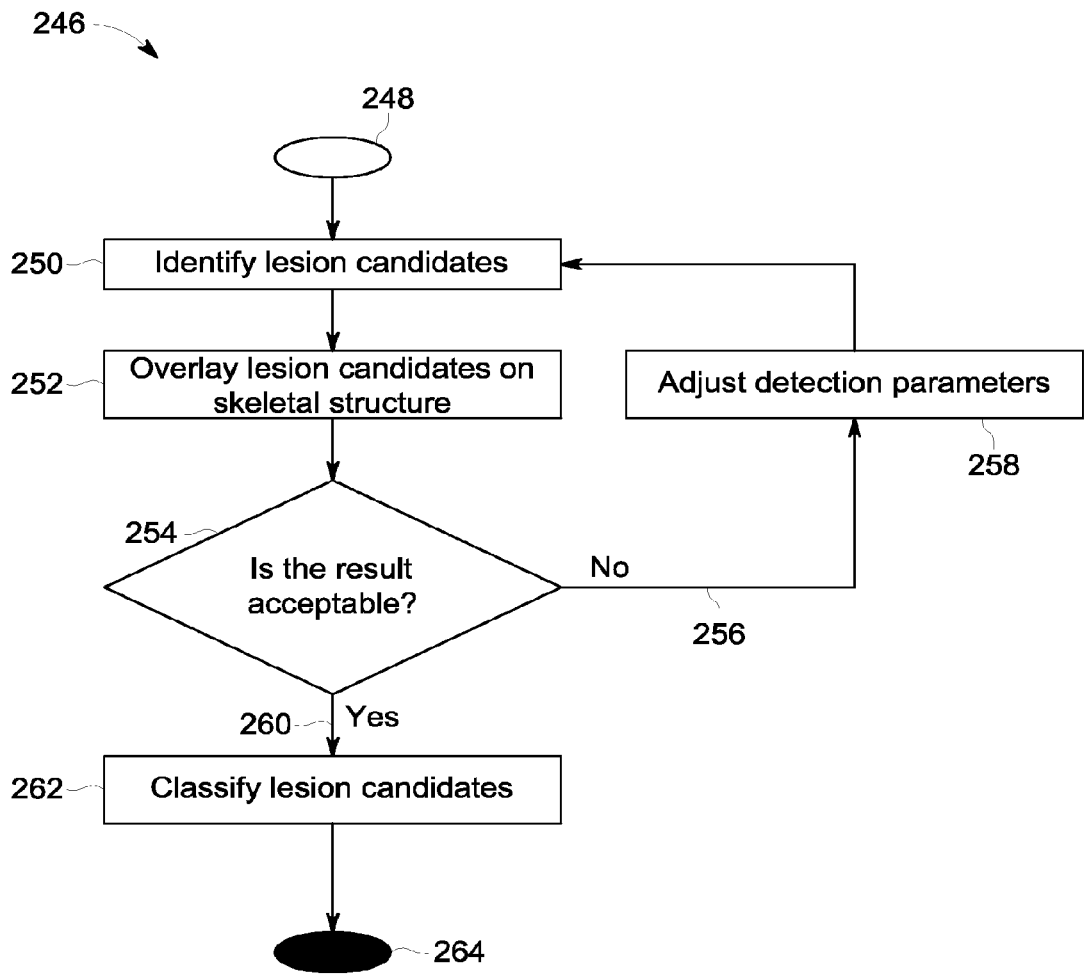
FIG. 6 is a flowchart setting forth the steps of a lesion detection subroutine of the technique of FIG. 4 according to one embodiment of the invention.

Referring again to FIG. 4, after the bone segmentation subroutine 210 of step 208 is complete, technique 200 continues to step 244 wherein technique 200 uses the segmented anatomical image data output from bone segmentation subroutine 210 and the functional image data selected at step 204 to detect bone lesions at using a lesion detection subroutine 246, as described in detail in FIG. 6.

Referring now to FIG. 6, the lesion detection subroutine 246 begins at step 248 by accessing the functional image data set corresponding to the image series selected at step 204 of technique 200. In step 250 lesion detection subroutine 246 automatically identifies possible lesion candidates in the functional image data set using a thresholding algorithm. In one embodiment, the possible lesion candidates are identified based on the standardize uptake values (SUV) of image voxels within the PET data series. For example, lesion candidates may be defined as regions of voxels having a mean SUV within a predetermined range of values. During step 250, lesion detection subroutine 246 also assigns bookmarks to the lesion candidates. According to various embodiments, the assigned bookmarks may be automatically assigned to lesion candidates by a computer processor, such as CPU 12 of FIG. 1, and/or manually assigned by a user. The bookmarks may include identifying information for the lesion candidates including for example, a unique lesion identifier and/or the positional coordinates for the respective lesion candidate.

Images of the lesion candidates are generated in step 252 and displayed as an overlay on the patient skeletal image generated from the segmented skeletal structure output from bone segmentation subroutine 210 of FIG. 5. In one embodiment, the segmented skeletal structure from a CT image series is projected into a PET image that includes the lesion candidates. In decision block 254, the results of the automated lesion candidate detection step are reviewed to determine if the result of the lesion candidate detection is acceptable. If the lesion detection is not acceptable 256, lesion detection subroutine 246 proceeds to step 258 in which the lesion detection parameters are adjusted. However, if the lesion detection is acceptable 260, lesion detection subroutine 246 is prompted to move on to step 262 and classify the identified lesion candidates as being either bone lesions (i.e., lesions located within the skeletal structure) or non-bone lesions (i.e., lesions not located in the skeletal structure).

While step 252 is described above as occurring prior to decision block 254, lesion detection subroutine 246 may perform step 252 after decision block 254 determines that the results of the lesion candidate identification is acceptable in alternative embodiments.

To assist with classifying lesion candidates as being either bone lesions or non-bone lesions at step 262, lesion detection subroutine 246 uses the segmented CT volume of step 208. In particular, lesion detection subroutine 246 compares the location of the lesion candidates to the location of the identified skeletal structure. Any lesion candidates that fall within the location of the skeletal structure are automatically identified as bone lesions and any lesion candidates that are outside location of the skeletal structure are automatically identified as non-bone lesions. Because lesion detection subroutine 246 automatically classifies lesions as being bone or non-bone based on the identified location of the lesion candidate with respect to the identified location of the patient's skeletal structure, lesion candidates may be correctly classified as being bone lesions with high accuracy. The bookmark information for the lesion candidates may be updated following lesion detection subroutine 246 to include information to indicate whether the lesion candidate is a bone lesion or a non-bone lesion. Further, data corresponding to the classified bone lesions may be combined and interpreted as a common object for quantitative analysis, rather than reviewing and determining quantitative data for each lesion separately. Lesion detection subroutine 246 ends at block 264.

Referring again to FIG. 4, the results of the lesion classification determined during lesion detection subroutine 246, as well as the bookmark information for the lesion candidates, are optionally output to a database for storage at step 266 (shown in phantom). Technique 200 also uses the results of the lesion classification in step 268 to calculate quantitative information regarding the skeletal structure and detected bone lesions of the patient. It is contemplated that quantitative information regarding the skeletal structure and detected bone lesions may be in regard to individual bone lesions or the total of all bone lesions, according to various embodiments. The quantitative information is displayed at step 270.

According to one embodiment, technique 200 calculates a patient skeletal metric that represents a total skeletal volume of the patient, a bone lesion metric that represents a total bone lesion volume of the patient, and a bone lesion index or lesion burden at step 268. The total skeletal volume is a quantitative value calculated based on the final bone segmentation output from bone segmentation subroutine 210 and represents the total volume of bone within the patient. The total bone lesion volume is a quantitative value calculated based on a total bone volume of the lesion candidates classified as bone lesions by lesion detection subroutine 246. According to one embodiment, the bone lesion index is calculated as a ratio of the total bone lesion volume to the total skeletal volume and is represented as a percentage. The bone lesion index quantifies the amount of disease in the patient's skeletal structure and represents a total tumor burden of the skeletal structure.

Figure 7:
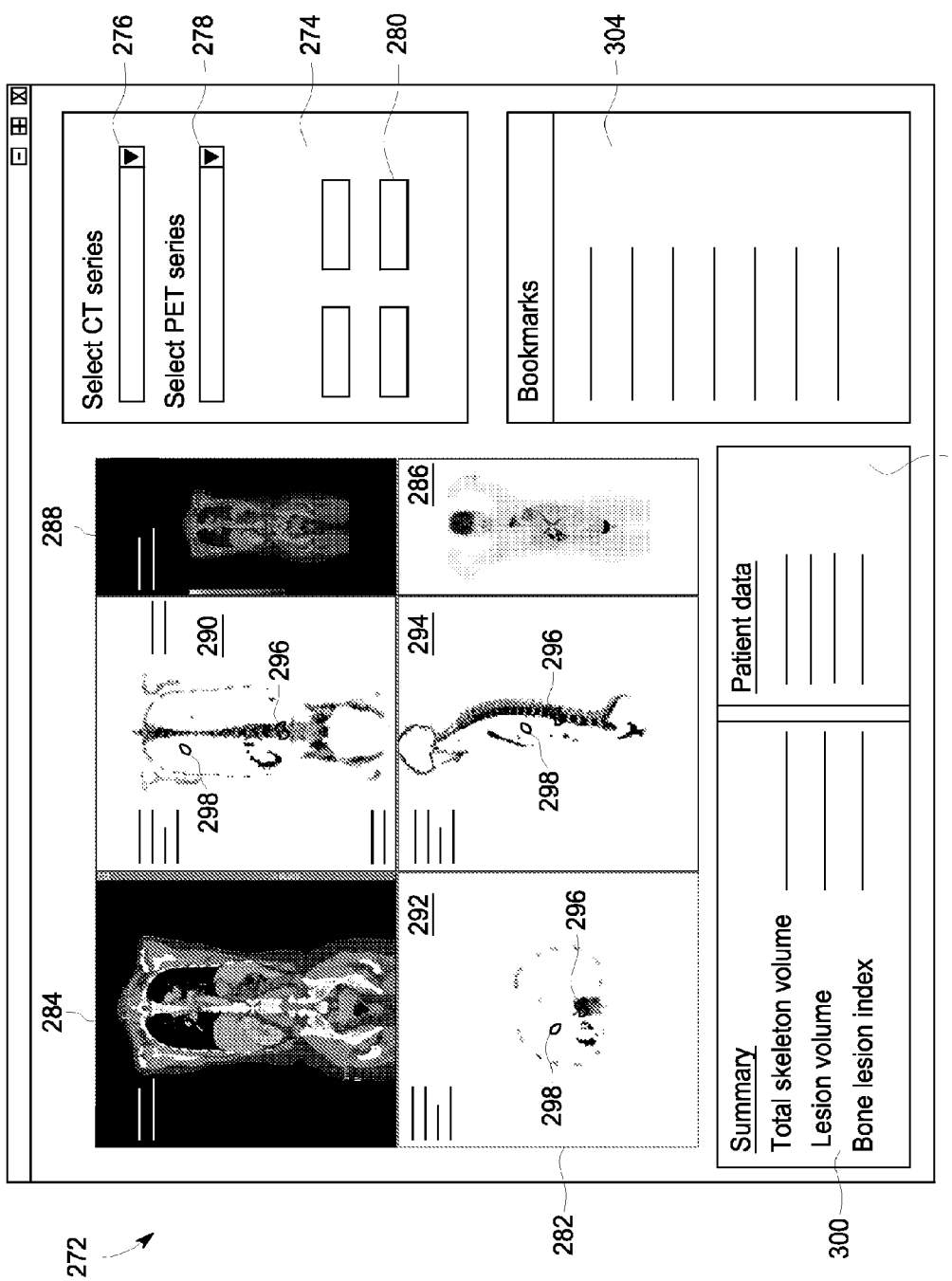
FIG. 7 illustrates an exemplary visual representation of a graphical user interface (GUI) for displaying a visualization of data in accordance with one embodiment of the present invention.

In some embodiments, portions of the selected anatomical and functional image series, visual representations of the lesion candidates, and the quantitative information calculated by technique 200 may be displayed on a graphical user interface (GUI) 272 as illustrated in FIG. 7. As shown, GUI 272 includes a menu display region 274, which contains an anatomical image selection menu 276, a functional image selection menu 278, and various command buttons 280. Anatomical image selection menu 276 and functional image selection menu 278 allow the user to select which multi-modality image series to load and analyze. According to various embodiments, command buttons 280 allow the user to interact with select steps of technique 200 and subroutines 210, 246. For example, one command button 280 may permit a user to adjust a segmentation parameter of segmentation subroutine 210 at step 214 or adjust lesion detection parameters of lesion detection subroutine 246 at step 258.

According to an exemplary embodiment, GUI 272 includes an image display region 282 that is separated into multiple windows in order to display multiple images. For example, image display 282 may include a first window 284 that displays a CT image, a second window 286 that displays a corresponding PET image, and a third window 288 that displays the CT image overlaid on the PET image. Fourth, fifth, and sixth windows 290, 292, 294 include various views of the segmented skeletal volume obtained from the CT image using bone segmentation subroutine 210 overlaid with contours of lesion candidates 296, 298 detected using lesion detection subroutine 246. In alternative embodiments, image display region 282 includes one or more selected images corresponding to the multi-modality image series and the detected lesions. Image display region 282 may further be configured to display bone lesions and non-bone lesions in different colors or with different shading to visually distinguish detected bone lesions from non-bone lesions. As one example, a lesion candidate classified as a bone lesion, such as lesion candidate 296, may be displayed with a red contour, and a lesion candidate classified as a non-bone lesion, such as lesion candidate 298, may be displayed with a blue contour.

According to various embodiments, image display region 282 may be configured as an interactive workspace to permit a user to interact with the images to perform various tasks including, for example, manually identify lesion candidates, delete an automatically identified lesion, and/or change the classification of an automatically detected lesion, as non-limiting examples.

Analysis display region 300 includes a visual display of the quantitative or statistical data computed in step 268 of technique 200. This data can include the total skeleton volume of the patient, the total volume of bone lesions and non-bone lesions, the total bone lesion volume (i.e., total tumor burden), the calculated bone lesion index, and other statistical information calculated during step 268. An information display region 302 is also located within in GUI 272 to provide the user with patient and scan information including, for example, name, age, the date of scans, and/or various parameters associated with the scans.

GUI 272 also includes a bookmark display region 304 that lists identifying information for the lesion candidates flagged by either the computer system or the user. According to various embodiments, bookmark display region 304 may include a unique identifier for a particular lesion candidate, the coordinates for that particular lesion candidate, and whether the particular lesion candidate is a bone-lesion or a non-bone lesion.

Optionally, one or more of regions 274, 282, 300, 302, and 304 may be configured as a control panel to permit a user to input and/or select data through input fields, dropdown menus, etc. It is noted that the arrangement of GUI 272 is provided merely for explanatory purposes, and that other GUI arrangements, field names, and visual outputs may take different forms within the scope of various embodiments of the invention. Additional display techniques may also include temperature gauges, graphs, dials, font variations, annotations, and the like.

A technical contribution for the disclosed method and apparatus is that it provides for a computer implemented system and method of detecting bone lesions using multi-modality image data.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

In accordance with one embodiment of the present invention, a non-transitory computer readable storage medium has stored thereon a computer program and represents a set of instructions that when executed by the computer causes the computer to access a first set of data of a first data type and a second set of data of a second data type. The first set of data is acquired from a patient with a first imaging modality, and the second set of data is acquired from the patient with a second imaging modality. The set of instructions also causes the computer to perform a segmentation on the first set of data to identify a subset of the first set of data corresponding to a skeletal structure of the patient. Further, the set of instructions causes the computer to automatically calculate a patient skeletal metric from the subset of the first set of data, the patient skeletal metric representing a total bone volume of the patient. In addition, the set of instructions causes the computer to detect at least one lesion in the second set of data, classify the at least one lesion as a one of a bone lesion and a non-bone lesion, and automatically calculate a bone lesion metric based on the classification. The set of instructions further causes the computer to calculate a lesion burden as a ratio of the bone lesion metric and the patient skeletal metric.

According to another embodiment of the invention, a method includes accessing an anatomical image data set acquired from a patient and accessing a function image data set acquired from the patient. The method also includes identifying a subset of the anatomical image dataset corresponding to bone and calculating a skeletal volume from the subset of the anatomical image dataset. In addition, the method includes identifying a set of lesions from the function image dataset, comparing the set of lesions to the subset of the anatomical image dataset to identify at least one bone lesion within the set of lesions, and automatically calculating a bone lesion burden based on the at least one bone lesion. Further, the method includes calculating a bone lesion index from the bone lesion burden and the skeletal volume.

According to yet another embodiment of the invention, a medical diagnostic tool includes an image acquisition system configured to acquire multi-modality image data, a first database having stored thereon a first image dataset acquired from a patient using a first imaging modality, a second database having stored thereon a second image dataset acquired from the patient using a second imaging modality, and a computer processor. The computer processor is programmed to access the first and second image datasets. The computer processor is further programmed to segment the first image dataset to define a set of skeletal data, identify a location of a lesion candidate in the second image set, compare the location of the lesion candidate to the set of skeletal data, and classify the lesion candidate as one of a bone lesion and a non-bone lesion based on the comparison to define a set of bone lesion data. In addition, the computer processor is programmed to calculate a lesion burden based on a ratio of the set of bone lesion data and the set of skeletal data. The medical diagnostic tool also includes a graphical user interface (GUI) constructed to display an image generated from overlaying a first image corresponding to the set of skeletal data on a second image corresponding to the set of bone lesion data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-transitory computer readable storage medium having a computer program stored thereon and representing a set of instructions that, when executed by a computer, causes the computer to:
   perform a segmentation on image data to identify a skeletal structure using a defined segmentation parameter;
   fill cavities on the identified skeletal structure in the image data, the cavities corresponding to bone marrow, a spinal cord, and a brain;
   detect a jaw-bone in the image data based on a ratio of bone to soft tissue; and
   remove the brain from the image data based on the detected jaw-bone.

2. The computer readable storage medium of claim 1, wherein the set of instructions further causes the computer to display a segmented image of the skeletal structure for review by a user to determine if the segmented image is an acceptable result of the segmentation.

3. The computer readable storage medium of claim 2, wherein, the set of instructions further causes the computer to determine if the segmented image is an acceptable result of the segmentation.

4. The computer readable storage medium of claim 3, wherein, if the segmented image is not an acceptable result, the set of instructions further causes the computer to determine if the segmented image is to be edited manually.

5. The computer readable storage medium of claim 3, wherein, if the segmented image is not an acceptable result, the set of instructions further causes the computer to adjust the segmentation parameter to perform the segmentation a second time.

6. The computer readable storage medium of claim 1, wherein the set of instructions further causes the computer to access the image data on which the segmentation is to be performed.

7. The computer readable storage medium of claim 6, wherein the set of instructions further causes the computer to display the image data to a user to enable the user to adjust the segmentation parameter.

8. The computer readable storage medium of claim 1, wherein the set of instructions further causes the computer to detect possible lesion candidates based on a thresholding algorithm.

9. The computer readable storage medium of claim 8, wherein the set of instructions further causes the computer to classify the possible lesion candidates as bone lesions or non-bone lesions.

10. A method comprising:
    performing a segmentation on image data to identify a skeletal structure using a defined segmentation parameter;
    filling cavities on the identified skeletal structure in the image data, the cavities corresponding to bone marrow, a spinal cord, and a brain;
    detecting a jaw-bone in the image data based on a ratio of bone to soft tissue; and
    removing the brain from the image data based on the detected jaw-bone.

11. The method of claim 10 further comprising displaying, via a computer, a segmented image of the skeletal structure for review by a user to determine if the segmented image is an acceptable result of the segmentation.

12. The method of claim 10 further comprising determining if the segmented image is an acceptable result of the segmentation.

13. The method of claim 12 further comprising, if the segmented image is not an acceptable result, determining if the segmented image is to be edited manually.

14. The method of claim 12 further comprising, if the segmented image is not an acceptable result, adjusting the segmentation parameter prior to performing the segmentation a second time.

15. The method of claim 10 further comprising accessing, using a computer, the image data on which the segmentation is to be performed.

16. The method of claim 15 further comprising displaying, via the computer, the image data to a user to enable the user to adjust the segmentation parameter.

17. The method of claim 10 further comprising detecting possible lesion candidates based on a thresholding algorithm.

18. The method of claim 17 further comprising classifying the possible lesion candidates as bone lesions or non-bone lesions.

19. An apparatus comprising:
    a computer processor programmed to:
        perform a segmentation on image data to identify a skeletal structure using a defined segmentation parameter;
        fill cavities on the identified skeletal structure in the image data, the cavities corresponding to bone marrow, a spinal cord, and a brain;
        detect a jaw-bone in the image data based on a ratio of bone to soft tissue; and
        remove the brain from the image data based on the detected jaw-bone.

20. The apparatus of claim 19 further comprising a graphical user interface of a computer to display a segmented image of the skeletal structure for review by a user to determine if the segmented image is an acceptable result of the segmentation.

* * * * *